(12) United States Patent
Biagini et al.

(10) Patent No.: US 9,257,236 B2
(45) Date of Patent: Feb. 9, 2016

(54) ORGANIC DYE FOR A DYE-SENSITIZED SOLAR CELL

(71) Applicants: ENI S.P.A., Roma (IT); Centre National de la Recherche Scientifique, Paris Cedex (FR)

(72) Inventors: Paolo Biagini, San Giuliano Terme (IT); Dora Demeter, Angers (FR); Philippe Leriche, Angers (FR); Andrea Pellegrino, Trecate (IT); Jean Roncali, La Fléche (FR); Giuliana Schimperna, Novara (IT)

(73) Assignees: Centre National de la Recherche Scientifique, Paris (FR); ENI S.P.A., Rome (IT)

(*) Notice: Subject to any disclaimer, the term of this patent is extended or adjusted under 35 U.S.C. 154(b) by 0 days.

(21) Appl. No.: 14/396,212

(22) PCT Filed: Apr. 19, 2013

(86) PCT No.: PCT/EP2013/058159
§ 371 (c)(1),
(2) Date: Oct. 22, 2014

(87) PCT Pub. No.: WO2013/160201
PCT Pub. Date: Oct. 31, 2013

(65) Prior Publication Data
US 2015/0129815 A1 May 14, 2015

(30) Foreign Application Priority Data
Apr. 23, 2012 (IT) .............................. MI2012A0674

(51) Int. Cl.
| | |
|---|---|
| H01G 9/20 | (2006.01) |
| H01L 51/00 | (2006.01) |
| C09B 57/00 | (2006.01) |
| C07D 333/08 | (2006.01) |

(52) U.S. Cl.
CPC ............ *H01G 9/2059* (2013.01); *C07D 333/08* (2013.01); *C09B 57/00* (2013.01); *H01L 51/0067* (2013.01); *H01L 51/0068* (2013.01); *H01G 9/2031* (2013.01); *Y02E 10/542* (2013.01); *Y02E 10/549* (2013.01)

(58) Field of Classification Search
CPC .......... C09B 1/00; C09B 15/00; C09B 29/00; H01L 31/00; H01L 51/0067; H01L 51/0068; H01L 51/0074
USPC ................................... 136/252, 263; 430/541
See application file for complete search history.

(56) References Cited

FOREIGN PATENT DOCUMENTS

| EP | 1311001 A1 | 5/2003 |
|---|---|---|
| KR | 20100136929 | * 12/2010 |
| WO | 2010147425 A2 | 12/2010 |

OTHER PUBLICATIONS

Machine translation of KR20100136929.*

Solution Processable Rhodanine-Based Small Molecule Organic Photovoltaic Cells with a Power Conversion Efficiency of 6.1%, Li et al., Adv. Energy Mater. 2012, 2, 74-77.*
International Search Report and Written Opinion dated Jul. 11, 2013 for PCT/EP2013/058159.
D.J. Milliron et al: "Electroactive Surfactant designed to mediate Electron Transfer between CdSe Nanocrystals and Organic Semiconductors", Adv.Mater., vol. 15. No. 1. 2003. pp. 58-61. XP002686997.
J. Warnan et al.: "Application of Poly(3-hexylthiophene) functionalized with an Anchoring Group in Dye-sensitized solar Cells", Macromol.Rapid Commun., vol. 32, 2011, pp. 1190-1194. XP002686998.
K. Tanaka et al.: "Development and Photovoltaic Performance of Oligothiophene-sensitized TiO2 Solar Cells", Chem. Lett., vol. 35, No. 6, 2006. pp. 592-593. XP002686999.
E. Miyazaki et al.: "Simple Oligothiophene-based Dyes for Dye-sensitized Solar Cells (DSSCs)", Bull.Chem. Soc.Jpn., vol. 84, No. 5, 2011, pp. 459-465. XP002687000.
N. Koumura et al.: "Alkyl-functionalized Organic Dyes for efficient Molecular Photovoltaics" JACS, vol. 128, 2006, pp. 14256-14257. XP002687001.
H.Choi et al.: "Highly efficient and thermally stable Organic Sensitizers for solvent-free Dye-Sensitized Solar Cells", Angew.Chem.Int. Ed., vol. 47, 2008, pp. 327-330. XP002687002.
Tan S. et al. "Novel Carboxylated Oligothiophenes as Sensitizers in Photoelectric Conversion Systems", Chemistry—A European Journal (2005), vol. 11, Issue 21, p. 6272-6276.
Mishra A. et al. "Metal-Free Organic Dyes for Dye-Sensitized Solar Cells: From Structure: Property Relationships to Design Rules", Angewandte Chemie (2009), vol. 48, p. 2474-2499.
Yang H. et al. "Organic Dyes Incorporating the Dithieno[3,2-b:2',3'-d]thiophene Moiety for Efficient Dye-Sensitized Solar Cells", Organic Letters (2010), vol. 12, No. 1, p. 16-19.
Sahu D. et al. "Synthesis and applications of novel acceptor-donor-acceptor organic dyes with dithienopyrrole- and fluorene-cores for dye-sensitized solar cells", Tetrahedron (2011), vol. 67, No. 2, p. 303-311.
Krömer J. et al. "Homologous series of regioregular alkylsubstituted oligothiophenes up to an 11-mer", Tetrahedron (2001), vol. 57, p. 3785-3794.
Roquet S. et al. "Triphenylamine-Thienylenevinylene Hybrid Systems with Internal Charge Transfer as Donor Materials for Heterojunction Solar Cells", Journal of American Chemical Society (2006), vol. 128, No. 10, p. 3459-3466.
Mikroyannidis J. A. et al. "Triphenylamine- and benzothiadiazole-based dyes with multiple acceptors for application in dye-sensitized solar cells", Journal of Power Sources (2010), vol. 195, Issue 9, p. 3002-3010.
Nazeeruddin M. K., "Conversion of light to electricity by cis-X2bis(2,2'-bipyridyl-4,4'-dicarboxylate)ruthenium(II) charge-transfer sensitizers (X = Cl-, Br-, I-, CN-, and SCN-) on nanocrystalline titanium dioxide electrodes", Journal of the American Chemical Society (1993), vol. 115, p. 6382-6390.
O'Regan & Gratzel. "A low-cost, high-efficiency solar cell based on dye-sensitized colloidal TiO2 films." Institute of Physical Chemistry, Swiss Federal Institute of Technology, Letters to Nature, vol. 353 (1991), p. 737-740.

* cited by examiner

*Primary Examiner* — Khanh Tuan Nguyen
*Assistant Examiner* — Haidung Nguyen
(74) *Attorney, Agent, or Firm* — Pearne & Gordon LLP

(57) ABSTRACT

Organic dye for a dye-sensitized solar cell (DSSC) comprising at least one electron-acceptor unit and at least one π-conjugated unit. Said organic dye is particularly useful in a dye-sensitized photoelectric transformation element which, in its turn, can be used in a dye-sensitized solar cell (DSSC).

5 Claims, No Drawings

ORGANIC DYE FOR A DYE-SENSITIZED SOLAR CELL

The present invention relates to an organic dye for a dye-sensitized solar cell (DSSC).

More in particular, the present invention relates to an organic dye for a dye-sensitized solar cell (DSSC) comprising at least one electron-acceptor unit and at least one π-conjugated unit.

Said organic dye is particularly useful in a dye-sensitized photoelectric transformation element which, in its turn, can be used in a dye-sensitized solar cell (DSSC).

Consequently, it is a further object of the present invention a dye-sensitized photoelectric transformation element comprising the organic dye above reported, as well as a dye-sensitized solar cell (DSSC) comprising said photoelectric transformation element.

Dye-sensitized solar cells (DSSCs) have been developed by Gratzel et al. on 1991 and they have attracted considerable attention in recent years due to their high efficiency and remarkably low manufacture cost compared to the existing silicon solar cells.

The dye-sensitized solar cells (DSSCs) are photoelectrochemical solar cells mainly comprising organic dye molecules capable of absorbing visible light to generate electron-hole pair, and transition metal oxide for transmitting the generated electrons.

As organic dyes for dye-sensitized solar cells (DSSCs), ruthenium metal complexes which show high photoelectric transformation efficiency has been widely used. However, ruthenium metal complexes contain expensive ruthenium metal and usually require careful synthesis and tricky purification steps.

Recently, it has been found that metal-free organic dyes which show excellent properties in terms of absorption efficiency, oxidation reduction stability and intramolecular charge-transfer (CT) absorption, may be used for dye-sensitized solar cells (DSSCs) as an alternative of expensive ruthenium metal complexes.

Metal-free organic dyes, generally, comprise electron donor unit—electron acceptor unit connected by π-conjugated unit. For most metal-free organic dyes, arylamine derivatives function as electron-donor unit and cyanoacrylic acid or rodhanine residue functions as electron acceptor unit, and they are connected by π-conjugated unit such as, for example, methanine unit or thiophene chain.

A lot of studies have been carried out with regard to said metal-free organic dyes.

For example, Tan S. et al. in the article "Novel Carboxylated Oligothiophenes as Sensitizers in Photoelectric Conversion Systems", *Chemistry—A European Journal* (2005), Vol. 11, Issue 21, pg. 6272-6276, disclose novel carboxylated oligothiophenes with different thiophene units as photosensitisers in dye-sensitized solar cells (DSSCs). It is said that the introduction of —COOH group into thiophene molecules may led to a red shift of UV-visible absorption, increase light-harvesting efficiency and enhance photoinduced charge transport by forming efficient covalent bonds to the substrate surface. It is also said that the dye-sensitized solar cells (DSSCs) based on said oligothiophenes have excellent performances: in particular, under irradiation of 100 mW·cm$^{-2}$ a short-circuit current of 10.57 mA·cm$^{-2}$ and an overall photoelectric transformation efficiency ($\eta$) of 3.36% is achieved, when pentathiophene dicarboxylated acid was used as a sensitizer.

Tanaka K. et al. in the article "Development and Photovoltaic Performance of Oligothiophene-sensitized TiO$_2$ Solar Cells", *Chemistry Letters* (2006), Vol. 35, No. 6, pg. 592-593, disclose novel dye-sensitized TiO$_2$ solar cells using a variety of oligothiophenecarboxylic acids. It is said that said solar cells show relatively high photovoltaic performances, i.e a photoelectric transformation efficiency ($\eta$) ranging from 0.41% to 1.29%, which are largely dependent on the chain lengths of the oligothiophenes and on the number of the carboxylic groups.

Mishra A. et al. in the review "Metal-Free Organic Dyes for Dye-Sensitized Solar Cells: From Structure: Property Relationships to Design Rules", *Angewandte Chemie* (2009), Vol. 48, pg. 2474-2499, disclose recent advances in molecular design and technological aspects of metal-free organic dyes for application in dye-sensitized solar cells (DSSCs). Special attention has been paid to the design principles of this organic dyes and on the effect of various electrolyte systems. Co-sensitization, an emerging technique to extend the absorption range, is also discussed as a way to improve the performance of the device. In addition, inverted organic dyes for photocatode are also disclosed, which constitute a relatively new approach for the production of tandem cells. Moreover, special consideration has been paid to the correlation between the molecular structure and the physical properties of the metal-free organic dyes with regard to their performances in dye-sensitized solar cells (DSSCs).

Yang H. et al. in the article "Organic Dyes Incorporating the Dithieno[3,2-b:2',3'-d]thiophene Moiety for Efficient Dye-Sensitized Solar Cells", *Organic Letters* (2010), Vol. 12, No. 1, pg. 16-19, disclose new dipolar compounds incorporating dithieno[3,2-b:2',3'-d]thiophene unit as the electron-donor, an oligothiophene as the conjugated spacer and 2-cyanoacrylic acid as the electron acceptor. These non-arylamine type metal-free organic compounds are said to be successfully used as the sensitizers of dye-sensitized solar cells (DSSCs): in particular, under AM 1.5 G irradiation the photoelectric transformation efficiency ($\eta$) ranges from of 3.54% to 5.15%.

Sahu D. et al. in the article "Synthesis and applications of novel acceptor-donor-acceptor organic dyes with dithienopyrrole- and fluorene-cores for dye-sensitized solar cells", *Tetrahedron* (2011), Vol. 67, No. 2, pg. 303-311, disclose new symmetrical organic dyes including a fluorene or a dithienopyrrole unit as electron donor, an oligothiophene as the conjugated spacer and two 2-cyanoacrylic acid groups as the electron acceptor. It is said that the dye-sensitized solar cells (DSSCs) comprising said organic dyes, in particular in the case of dyes including a fluorene unit, have a photoelectric transformation efficiency ($\eta$) of 4.73% under irradiation of 100 mW·cm$^{-2}$ and a maximum incident photon conversion efficiency (IPCE) of about 76% under AM 1.5 simulated solar irradiance.

Warnan J. et al. in the article "Application of Poly(3-hexylthiophene) Functionalized with an Anchoring Group in Dye-sensitized Solar Cells", *Macromolecular Rapid Communication* (2011), Vol. 32, DOI: 10.1002/marc.201100214, disclose a series of three poly(3-hexylthiophene) functionalized either with a cyanoacetic acid (CA) or a rhodanine-3-acetic acid anchoring groups, which were synthesized and characterized. The titanium dioxide (TiO$_2$) based dye-sensitized solar cells (DSSCs) have been fabricated and performances were tested. It is said that the dye-sensitized solar cells (DSSCs) comprising said poly(3-hexylthiophene) show a photoelectric transformation efficiency ($\eta$) of 3.02% under irradiation of 100 mW·cm$^{-2}$ and a maximum incident photon conversion efficiency (IPCE) of about 50% under AM 1.5 simulated solar irradiance.

However, most of the organic dyes already known may exhibit low photoelectric transformation efficiency ($\eta$) compared to ruthenium metal complex dyes. Therefore, there have been continuous attempts to develop novel organic dyes able to give dye-sensitized solar cells (DSSCs) having improved photoelectric transformation efficiency ($\eta$) compared to the existing organic dyes.

The Applicant has faced the problem of finding an organic dye able to give dye-sensitized solar cells (DSSCs) having improved photoelectric transformation efficiency ($\eta$), i.e. a photoelectric transformation efficiency ($\eta$) higher than or equal to 7.5%.

The Applicant has found an organic dye comprising at least one electron-acceptor group and at least one $\pi$-conjugated unit which is able to give a dye-sensitized solar cell (DSSC) having improved photoelectric transformation efficiency ($\eta$), i.e. a photoelectric transformation efficiency ($\eta$) higher than or equal to 7.5%. Moreover, said dye-sensitized solar cells (DSSCs) also have improved Voc (open circuit photovoltage), FF (fill factor) and Jsc (short-circuit photocurrent density).

An object of the present invention therefore relates to an organic dye having general formula (I):

$$X\text{-}(T)_n\text{-}Y\text{-}(T)_n\text{-}Z \quad (I)$$

wherein:

X and Z, equal to or different from each other, represent a hydrogen atom; or are selected from the following groups: a —COOH group, a phosphonic group having formula —PO(OH)$_2$ or —PO(OH)(R$_1$) wherein R$_1$ represents a C$_1$-C$_{16}$, preferably C$_2$-C$_8$, alkyl group, linear or branched, a carboxycyanovinylene group having formula (II) or (III):

(II)

(III)

wherein R$_2$ and R$_3$, equal to or different from each other, represent an hydrogen atom, or are selected from C$_1$-C$_{16}$, preferably C$_2$-C$_8$, alkyl groups linear or branched; with the provision that at least one of X and Z is not an hydrogen atom;

T represents a 2,5-thienylene group having general formula (IV):

(IV)

wherein R$_4$ and R$_5$, equal to or different from each other, represent an hydrogen atom; or are selected from: C$_4$-C$_{20}$, preferably C$_5$-C$_{12}$, alkyl groups, linear or branched, saturated or unsaturated, optionally containing heteroatoms, C$_4$-C$_{12}$, preferably C$_5$-C$_8$, cycloalkyl groups, optionally substituted, C$_4$-C$_{11}$, preferably C$_5$-C$_7$, heterocyclic groups, optionally substituted, C$_3$-C$_{20}$, preferably C$_3$-C$_{12}$, trialkylsilyl groups; with the provision that at least one of R$_4$ and R$_5$ is not an hydrogen atom;

n is an integer ranging from 2 to 7;

Y represents a divalent organic aromatic or heteroaromatic group having electron-donor properties.

For the aim of the present invention and of the following claims, the definitions of the numerical ranges always comprise the extremes unless otherwise specified.

In accordance with a preferred embodiment of the present invention, in said general formula (I), Y may be selected from the groups having general formulae (V), (VI), (VII), (VIII), (IX), (X), (XI), (XII), (XIII), (XIV), (XV), (XVI), (XVII), (XVIII), (XIX):

(V)

(VI)

(VII)

(VIII)

(IX)

(X)

(XI)

(XII)

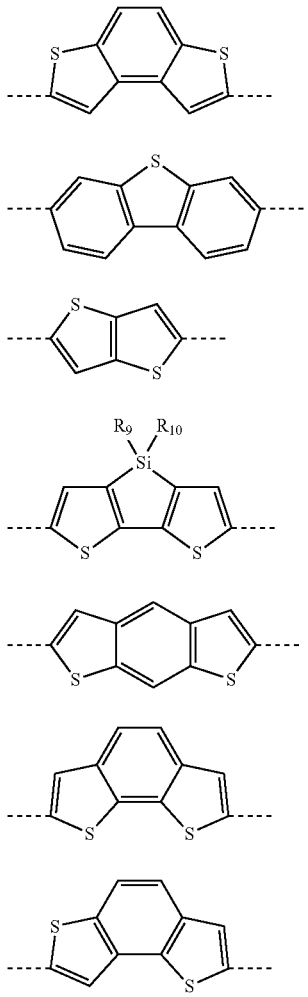

wherein $R_6$, $R_7$, $R_8$, $R_9$ and $R_{10}$, equal to or different from each other, represent an hydrogen atom; or are selected from: $C_1$-$C_{30}$, preferably $C_1$-$C_{20}$, alkyl groups, linear or branched, saturated or unsaturated, $C_4$-$C_{12}$, preferably $C_5$-$C_8$, cycloalkyl groups optionally substituted; said Y groups having general formulae (V)-(XIX) being optionally substituted with one or more groups selected from $C_1$-$C_{30}$, preferably $C_1$-$C_{20}$, alkyl groups, linear or branched, saturated or unsaturated, $C_4$-$C_{12}$, preferably $C_5$-$C_8$, cycloalkyl groups optionally substituted.

In accordance with a preferred embodiment of the present invention, in said general formula (I):

X is a hydrogen atom;

Z is a carboxycyanovinylene group having formula (II):

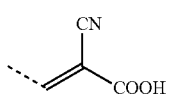
(II)

T represents a 2,5-thienylene group having general formula (IV):

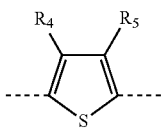
(IV)

wherein $R_4$ is a hydrogen atom and $R_5$ is a n-hexyl group or a n-octyl group;

n is 3;

Y is a divalent heteroaromatic group having general formula (V) or (VI):

The organic dye having general formula (I) may be prepared by processes known in the art, for example, by the nickel-catalyzed cross-coupling of Grignard reagent of alkyl bromothiophene and α-α'-dibromo-oligothiophenes, such as described, for example, by Krömer J. et al. in the article "Homologous series of regioregular alkylsubstituted oligothiophenes up to an 11-mer", *Tetrahedron* (2001), Vol. 57, pg. 3785-3794; or by the Vilsmaier-Heck formilation of thiophene groups, such as described, for example, by Roquet S. et al. in the article "Triphenylamine-Thienylenevinylene Hybrid Systems with Internal Charge Transfer as Donor Materials for Heterojunction Solar Cells", *Journal of American Chemical Society* (2006), Vol. 128, No. 10, pg. 3459-3466; or by the reaction of formil derivatives with cyanoacetic acid such as described, for example, by Mikroyannidis J. A. et al. in the article "Triphenylamine- and benzothiadiazole-based dyes with multiple acceptors for application in dye-sensitized solar cells", *Journal of Power Sources* (2010), Vol. 195, Issue 9, pg. 3002-3010.

According to a further aspect, the present invention relates to a dye-sensitized photoelectric transformation element comprising at least one organic dye having general formula (I), said dye-sensitized photoelectric transformation element being supported on oxide semiconductor particles.

The photoelectric transformation element according to the present invention may be prepared by a process for preparing a dye-sensitized photoelectric transformation element for dye-sensitized solar cells (DSSCs) of the prior art, except of using the organic dye having general formula (I).

Preferably, the photoelectric transformation element according to the present invention, is prepared by forming oxide semiconductor thin film on a substrate and subsequently supporting the organic dye having general formula (I) on the thin film.

The substrate on which the oxide semiconductor thin film is formed preferably has a conductive surface, and is commercially available. Preferably, said substrate may be selected, for example, from: glass; transparent polymers such as, for example, polyethyleneterephthalate, polyethersulfone, or mixtures thereof. Preferably, said substrate may have conductivity lower than or equal to 1000Ω, more preferably lower than or equal to 100Ω.

As the oxide semiconductor particles, metal oxide is preferable. Preferably, said oxide semiconductor may be selected, for example, from: titanium dioxide, tin oxide, zinc oxide, tungsten oxide, zirconium oxide, gallium oxide, indium oxide, yttrium oxide, niobium oxide, tantalum oxide, vanadium oxide, or mixtures thereof. More preferably, titanium dioxide, tin oxide, zinc oxide, niobium oxide, indium oxide, or mixtures thereof, may be used, titanium dioxide, zinc oxide or tin oxide, or mixtures thereof, may be even more preferable, and titanium dioxide may be most preferable.

The oxide semiconductor particles may preferably have an average diameter ranging from 1 nm to 500 nm, more preferably ranging from 1 nm to 100 nm, and those having large diameter and those having small diameter may be mixed, or used in multi-layers.

The oxide semiconductor thin film may be prepared by means of different know techniques such as, for example: by spraying oxide semiconductor particles to form a thin film thereof directly on a substrate; by electrically depositing a semiconductor particle thin film using a substrate as an electrode; by applying semiconductor particle slurry or paste containing particles obtained by hydrolysis of suitable precursors such as a metal halogenide or a metal alkoxide, on a substrate ("doctor-blade" technique), and drying, curing or sintering. Preferably, paste may be applied on a substrate, and in this case, slurry may be obtained by dispersing semiconductor oxide particles, with particle diameter ranging from 1 nm to 200 nm, in a dispersion medium by a method known in the art.

As the dispersion medium, those capable of dispersing semiconductor particles may be used without limitation. Preferably, said dispersion medium may be selected, for example, from: water; alcohols such as, for example, ethanol; ketones such as, for example, acetone, acetylacetone; hydrocarbons such as, for example, hexane; or mixtures thereof. Water may be preferable because it minimizes change in viscosity of slurry. Optionally, a dispersion stabilizer may be used in order to stabilize the dispersion of the oxide semiconductor particles. Preferably, said dispersion stabilizer may be selected, for example, from: acids such as, for example, acetic acid, hydrochloric acid, nitric acid, acrylic acid; ketones such as, for example, acetylacetone; glycols such as, for example, polyethyleneglycol; alcohols such as, for example, polyvinylalcohol; or mixtures thereof.

The substrate on which slurry is applied may be sintered, and the sintering temperature may be higher than or equal to 100° C., preferably higher than or equal to 200° C. In any case, the upper limit of the sintering temperature may be the melting point or the softening point of the substrate, commonly 900° C., preferably 600° C. The sintering time may not be specifically limited, but preferably within 4 hours.

The thickness of the thin film on the substrate may ranges from 1 μm to 200 μm, preferably may ranges from 1 μm to 50 μm. The oxide semiconductor thin film may be subjected to a secondary treatment. For example, the thin film may be immersed in a solution of alkoxide, chloride, nitride, or sulfide, of the metal identical to the semiconductor, and dried or re-sintered, thereby improving the property of the thin film. The metal alkoxide may be selected, for example, from: titanium ethoxide, titanium isopropoxide, titanium t-butoxide, n-dibutyl-diacetyl tin, or mixtures thereof. Preferably, an alcohol solution of said metal alkoxide may be used. The metal chloride may be selected, for example, from: titanium tetrachloride, tin tetrachloride, zinc chloride, or mixtures thereof. Preferably, an aqueous solution of said metal chloride may be used. Thus obtained oxide semiconductor thin film may be comprised of oxide semiconductor particles.

The method for supporting organic dye on oxide semiconductor particles in the form of a thin film may not be specifically limited, and for example, a substrate having the oxide semiconductor thin film formed thereon may be immersed in a solution obtained by dissolving the organic dye having general formula (I) in a solvent capable of dissolving the same, or in a dispersion obtained by dispersing said organic dye having general formula (I). The concentration of the solution or of the dispersion, may be appropriately determined. Immersion temperature may range from −60° C. to 100° C., preferably from 0° C. to 50° C., more preferably is room temperature (25° C.), and immersion time may range from about 1 minute to 48 hours, preferably from 1 hour to 26 hours. The solvent used for dissolving the organic dye may be selected, for example, from: methanol, ethanol, acetonitrile, dichloromethane, dimethylsulfoxide, dimethylformamide, acetone, t-butanol, or mixtures thereof. Usually, the concentration of the solution may range from $1 \times 10^{-6}$ M to 1 M, preferably from $1 \times 10^{-5}$ M to $1 \times 10^{-1}$ M. Thus, a dye-sensitized photoelectric transformation element comprising oxide semiconductor particles on a dye-sensitized thin film, may be obtained.

Optionally, the organic dye having general formula (I) may be mixed with other organic dyes or metal complex dyes. The metal complex dyes that may be mixed may include, although not specifically limited, ruthenium complex or quaternary salt thereof, phthalocyanin, porphyrin; and the other organic dyes that may be mixed may include metal-free phthalocyanin, porphyrin, cyanin, merocyanin, oxonol, or triphenylmethane dye, methyne dye such as acrylate dyes described in European Patent Application EP 1,311,001, xanthenes, azo, anthraquinone, perylene dye (as described, for example by Nazeeruddin M. K., in *Journal of the American Chemical Society* (1993), Vol. 115, pag. 6382-6390). In case two or more kinds of organic dyes are used in combination, they may be sequentially absorbed in a semiconductor thin layer, or mixed, dissolved and absorbed.

In order to prevent aggregation of the organic dye on the oxide semiconductor thin layer, optionally, the organic dye having general formula (I), may be mixed with an inclusion compound: the obtained mixture may be adsorbed on a semiconductor thin layer. The inclusion compound may be selected, for example, from: cholic acids such as deoxycholic acid, dehydrodeoxycholic acid, kenodeoxycholic acid, cholic acid methyl ester, cholic acid sodium; polyethyleneoxides; crown ethers; cyclodextrins; calyxarenes; polyethyleneoxides; or mixtures thereof.

After the organic dye is supported, the surface of a semiconductor electrode may be treated with a compound which can be selected from: amine compounds such as, for example, 4-t-butyl pyridine; alcohols such as, for example, methanol, ethanol, butanol, or mixtures thereof; organic acids such as, for example, acetic acid, propionic acid, or mixtures thereof; or mixtures thereof. For example, a substrate having a dye-supported semiconductor particle thin film formed thereon may be immersed in an ethanol solution of amine.

According to a further aspect, the present invention also relates to a dye-sensitized solar cell (DSSC) comprising the dye-sensitized photoelectric transformation element above disclosed.

Said dye-sensitized solar cell (DSSC) may be prepared by methods know in the art of preparing a solar cell using photoelectric transformation element of the prior art, except of using a dye-sensitized photoelectric transformation element comprising oxide semiconductor particles where the organic dye having general formula (I) is supported. The dye-sensitized solar cell (DSSC) may comprise a photoelectric transformation element electrode (negative electrode) wherein the organic dye having general formula (I) is supported on the oxide semiconductor particles, a counter electrode (positive electrode), redox electrolyte, hole-transport material, or p-type semiconductor.

Preferably, the dye-sensitized solar cell (DSSC) according to the present invention may be prepared by coating titanium dioxide paste on a transparent conductive substrate; sintering the coated substrate to form a titanium dioxide thin film; immersing the substrate having titanium dioxide thin film formed thereon in a mixed solution in which the organic dye having general formula (I) is dissolved, so as to form a dye-absorbed titanium dioxide film electrode; providing a second transparent conductive substrate having a counter electrode formed thereon; forming a hole penetrating the second transparent conductive substrate and the counter electrode; placing thermoplastic polymer film between the counter electrode and the dye-absorbed titanium dioxide film electrode and heat-pressing them to join the counter electrode and the titanium dioxide film electrode; injecting electrolyte into the thermoplastic polymer film placed between the counter electrode and the titanium dioxide film electrode through the hole; and, sealing the hole with suitable materials which may be selected, for example, from thermoplastic polymers.

The redox electrolyte, hole-transport material, or p-type semiconductor may be liquid, a coagulated form (gel and gel phase), solid. The liquid may be selected, for example, from those obtained by dissolving redox electrolyte, dissolved salt, hole-transport material, or p-type semiconductor in a solvent, and a room temperature dissolved salt. The coagulated form (gel and gel phase) may be selected, for example, from those obtained by including redox electrolyte, a dissolved salt, hole-transport material, or p-type semiconductor in a polymer matrix or low molecular gellant. The solid may be selected, for example, from redox electrolyte, a dissolved salt, hole-transport material, or p-type semiconductor.

The hole-transport material may be selected, for example, from: amine derivatives; conductive polymers such as, for example, polyacetylene, polyaniline, polythiophene; or discotic liquids crystal phase such as, for example, triphenylene. The p-type semiconductor may be selected, for example, from CuI, CuSCN. As the counter electrode, those having conductivity and catalytic function on reduction of redox electrolyte may be preferably used, and, for example, those obtained by depositing platinum, carbon, rhodium, ruthenium, on a glass or a polymer film, or applying conductive particles thereon may be used.

The redox electrolyte used in the dye-sensitized solar cell (DSSC) according to the present invention may include halogen redox electrolyte comprising halogen compounds comprising halogen ion as a counter ion and a halogen molecule; metal redox electrolytes such as ferrocyanide-ferrocyanide or ferrocene-ferricynium ion; metal complexes such as cobalt complexes; organic redox electrolytes such as, for example, alkylthio-alkyldisulfide, viologen dye, hydroquinone-quinone; halogen redox electrolytes may be preferable. As the halogen molecule comprised in the halogen redox electrolyte, an iodine molecule may be preferable. As the halogen compounds comprising halogen ion as counter ion, a halogenated metal salt such as, for example, LiI, NaI, KI, $CaI_2$, $MgI_2$, CuI, or an organic ammonium salt of halogen such as, for example, tetraalkylammonium iodide, imidazolium iodide, pyridium iodide, or $I_2$ may be used.

In case the redox electrolyte is in the form of a solution comprising the same, an electrochemically inert solvent may be used. For example, acetonitrile, propylenecarbonate, etylenecarbonate, 3-methoxypropionitrile, methoxy-acetonitrile, valeronitrile, ethyleneglycol, propyleneglycol, diethyleneglycol, triethyleneglycol, butyrolactone, dimethoxyethane, dimethylcarbonate, 1,3-dioxolane, methylformate, 2-methyltetrahydrofurane, 3-methoxy-oxazolidin-2-on, sulforane, tetrahydrofurane, water, may be used. Acetonitrile, valeronitrile, propylenecarbonate, ethylenecarbonate, 3-methoxypropionitrile, ethyleglycol, 3-methoxy-oxazolidin-2-on, or butyrolactone, may be preferable. Said solvents may be used alone or in combination.

As a gel phase positive electrolyte, those obtained by including electrolyte or electrolyte solution in oligomer or polymer matrix, or including electrolyte or electrolyte solution in a starch gellant, may be used.

The concentration of the redox electrolyte may preferably ranges from 0.01% by weight to 99% by weight, and more preferably from 0.1% by weight to 30% by weight, with respect to the total weight of the solution.

The dye-sensitized solar cell (DSSC) according to the present invention may be obtained by disposing a photoelectric transformation element (negative electrode) wherein the organic dye is supported on oxide semiconductor particles on a substrate and a counter electrode (positive electrode) opposite thereto, and filling a redox electrolyte containing solution therebetween.

The present invention will be further illustrated below by means of the following examples which are given for purely indicative purposes and without any limitation of this invention.

EXAMPLES

Reagents and Materials

The reagents and materials used in the following examples, as well as their manufacturers, have been below reported:
magnesium turnings (Aldrich): used as such;
anydrous diethyl ether (Aldrich): used as such;
2-bromo-3-octyl-thiophene (Aldrich): used as such;
dibromoethane (Aldrich): used as such;
dibromothiophene (Aldrich): used as such;
[1,3-bis(diphenylphosphino)propane]dichloronickel(II) (Aldrich): used as such;
hydrochloric acid (Carlo Erba): used as such;
diethyl ether (Aldrich): used as such;
petroleum ether (Aldrich): used as such;
chloroform (Aldrich): used as such;
acetic acid (Aldrich): used as such;
N-bromosuccinimmide (Aldrich): used as such;
dichloromethane (Aldrich): used as such;
sodium bicarbonate (Aldrich): used as such;
anhydrous sodium sulfate (Aldrich): used as such;
anhydrous magnesium sulfate (Aldrich): used as such;
phosphorous oxychloride (Aldrich): used as such;
dimethylformamide (Aldrich): used as such;
cyanoacetic acid (Aldrich): used as such;
ammonium acetater (Aldrich): used as such;
glacial acetic acid (Aldrich): used as such;
methanol (Carlo Erba): used as such;
ethanol (Carlo Erba): used as such;
titanium tetyrachloride (Aldrich): used as such;
N-methyl-N-butylimidazolium iodide (Aldrich): used as such;
iodine (Carlo Erba): used as such;

lithium iodide (Aldrich): used as such;
guanidinium-thiocyanate (Aldrich): used as such;
tert-butylpyridine (Aldrich): used as such;
valeronitrile (Aldrich): used as such;
acetonitrile (Carlo Erba): used as such.

In the following examples the characterization methods below reported have been used.

NMR Spectra

The NMR spectra of the obtained compounds have been carried out with a spectrometer NMR Bruker Avance 400.

To this aim, about 10 mg of the sample to be examined have been dissolved in about 0.8 ml of a suitable deuterated solvent directly on the glass pipe used for the measurement. The chemical shifts scale has been calibrated with respect to the tetramethylsilane signal set to 0 ppm.

Mass Spectra

The mass spectra of the compounds obtained have been carried out with a reverse-geometry double-focusing spectrometer AT 95S DCI ("Desorption Chemical Ionization") with iso-butane as reagent gas in ions positive mode. The filament emission current has been calibrated at 0.1 mA with an electron beam energy equal to 100 eV and with a ions source temperature kept to 90° C.

Example 1

Synthesis of carboxycyanovinylen-[3,3',3'',3''',3'''', 3''''']-hexaoctyl-2,5':2',5'':2'',2''':5''',2'''':5'''', 2''''''-heptathiophene having general formula (Ia)

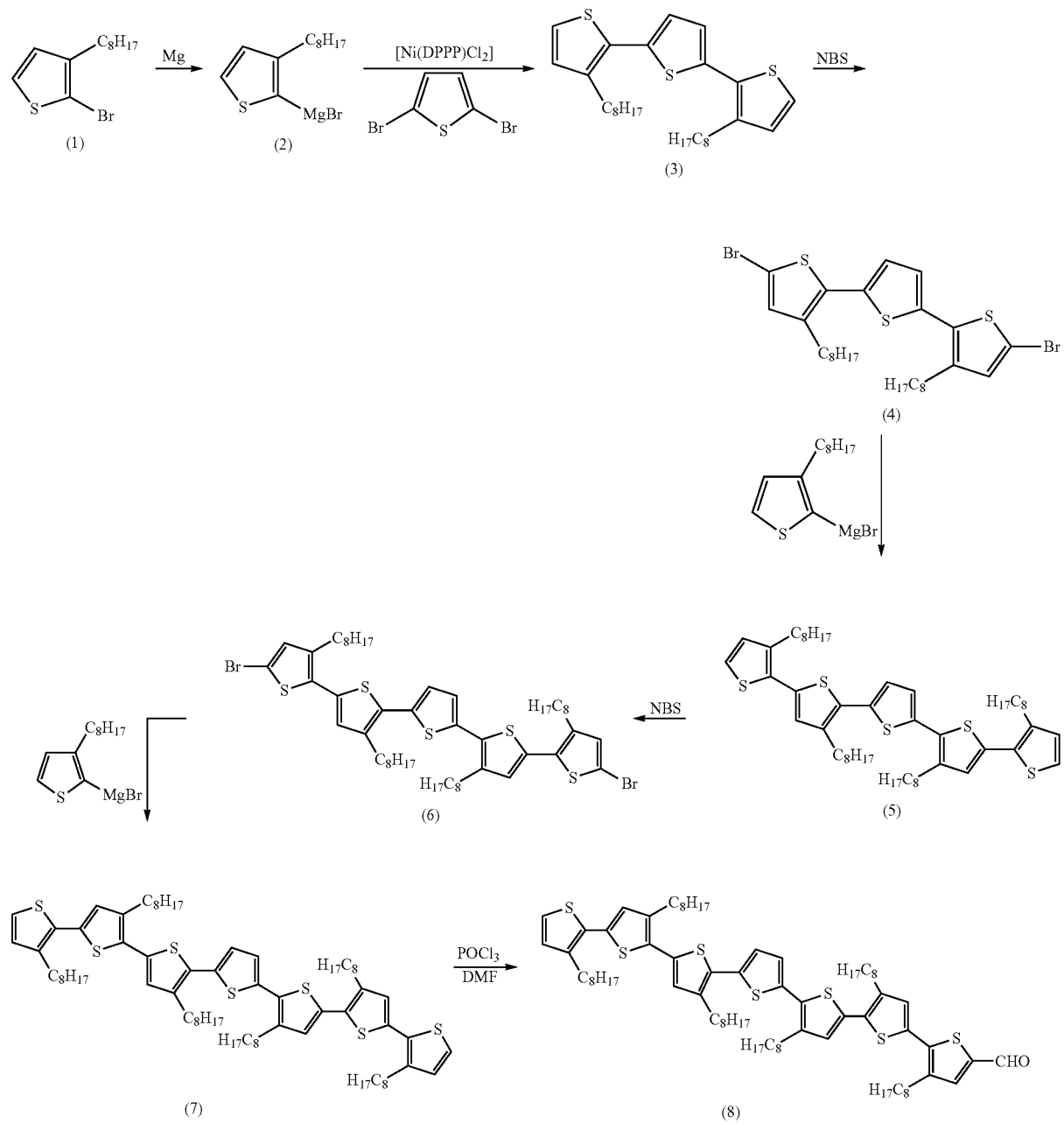

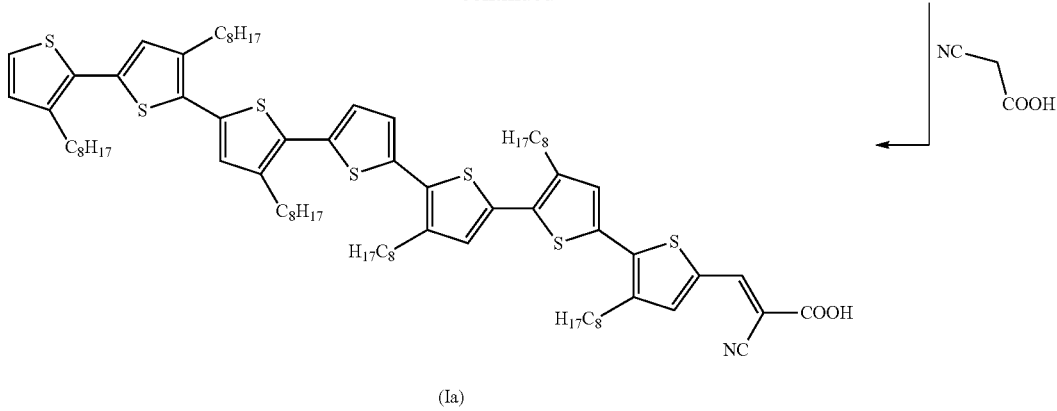

(Ia)

0.53 g (21.8 mmol) of magnesium turnings were introduced in a 100 ml flask and suspended in 30 ml of anhydrous diethyl ether. To the resulting suspension, maintained under an argon (Ar) atmosphere, was slowly added a solution of 3.0 g (3.9 mmol) of 2-bromo-3-octylthiophene having formula (1) and 0.93 ml (10.9 mmol) of dibromoethane in 20 ml of anhydrous diethyl ether. The obtained reaction mixture was sonicated for 30 minutes and subsequently heated at the boiling point of the solvent, for 1.5 hours. After the elimination of the excess of magnesium turnings by filtration, the solution containing 2-(3-octylthienyl)magnesium bromide having formula (2), was slowly added, at 0° C., to a mixture of 0.4 ml (3.6 mmol) of 2,5-dibromothiophene and 0.18 g (0.3 mmol) of [1,3-bis(diphenylphosphino)propane]dichloronickel(II) [Ni(DPPP)Cl$_2$] in 30 ml of anhydrous diethyl ether. The resulting reaction mixture was heated at the boiling point of the solvent, for 18 hours, and poured into a mixture of crushed ice and hydrochloric acid (HCl) (2 M) obtaining an organic phase and an aqueous phase which were separated. The aqueous phase was then extracted with diethyl ether (3×20 ml). The overall organic phase (obtained by joining the organic phases obtained as described above) was dried over anhydrous magnesium sulfate (MgSO$_4$), at room temperature (25° C.), for 3 hours. The solvent was subsequently evaporated at reduced pressure and the obtained residue was purified by chromatography on silica gel using petroleum ether as eluent obtaining 1.24 g (67% yield) of 3,3"-dioctyl-2,2':5',2"-terthiophene having formula (3), as yellow liquid, which was characterized by $^1$H NMR (300 MHz, CDCl$_3$) obtaining the following spectrum: 7.18 (d, 2H), 7.05 (s, 2H), 6.94 (d, 2H), 2.77 (t, 4H), 1.65-1.59 (m, 4H), 1.39-1.26 (m, 20H), 0.87 (t, 6H).

In a 100 ml flask, were introduced 1.24 g (2.6 mmol) of 3,3"-dioctyl-2,2':5',2"-terthiophene having formula (3) obtained as reported above and 60 ml of a mixture of chloroform and acetic acid (1:1 vol.). Subsequently, 0.98 g (5.6 mmol) of N-bromosuccinimide (NBS) were added, in small portions, to the resulting solution, at 0° C. The resulting reaction mixture was stirred at room temperature (25° C.), for 3 hours, and subsequently poured into water and extracted with dichloromethane (CH$_2$Cl$_2$) (3×20 ml). The overall organic phase (obtained by joining the organic phases obtained as described above) were thoroughly washed with water, aqueous sodium bicarbonate, brine and again with water, and subsequently dried over anhydrous sodium sulfate (Na$_2$SO$_4$). The solvent was subsequently evaporated at reduced pressure and the obtained residue was purified by chromatography on silica gel using petroleum ether as eluent obtaining 1.6 g (97% yield) of 5,5"-dibromo-3,3"-dioctyl-2,2':5',2"-terthiophene having formula (4), as yellow oil, which was characterized by $^1$H NMR (300 MHz, CDCl3) obtaining the following spectrum: 6.97 (s, 2H), 6.89 (s, 2H), 2.69 (t, 4H), 1.65-1.57 (m, 4H), 1.26 (m, 20H), 0.87 (t, 6.8 Hz, 6H).

In a 100 ml flask, were introduced 1.34 g (2.12 mmol) of 5,5"-dibromo-3,3"-dioctyl-2,2':5',2"-terthiophene having formula (4) obtained as reported above, 0.08 g (0.15 mmol) of [1,3-bis(diphenylphosphino)propane]-dichloronickel(II) [Ni(DPPP)Cl$_2$] and 30 ml of anhydrous diethyl ether. To the resulting solution were added, dropwise, 30 ml of an anhydrous diethyl ether solution containing 6.4 mmol of 2-(3-octylthienyl)magnesium bromide having formula (2) obtained as reported above. The resulting reaction mixture was heated at the boiling point of the solvent, for 20 hours, subsequently cooled to room temperature (25° C.) and quenched with 10 ml of hydrochloric acid (HCl) (1 M), followed by the addition of 50 ml of water. The obtained mixture was extracted with dichloromethane (CH$_2$Cl$_2$) (3×20 ml) and the overall organic phase (obtained by joining the organic phases obtained as described above) were washed with water, brine and dried over anhydrous magnesium sulfate (MgSO$_4$). The solvent was subsequently evaporated at reduced pressure and the obtained residue was purified by chromatography on silica gel using petroleum ether as eluent obtaining 1.47 g (82% yield) of 3,3',3''',3''''-tetraoctyl-2,5':2',5":2",2''':5''',2''''-pentathiophene having formula (5), as a golden oil which was characterized by $^1$H NMR (300 MHz, CDCl$_3$) obtaining the following spectrum: 7.17 (d, 2H), 7.08 (s, 2H), 6.95 (s, 2H), 6.94 (d, 2H), 2.78 (t, 8H), 1.17-1.59 (m, 8H), 1.33-1.28 (m, 40H), 0.88 (m, 12H).

In a 100 ml flask, were introduced 1.47 g (1.7 mmol) of 3,3',3''',3''''-tetraoctyl-2,5':2',5":2",2''':5''',2''''-pentathiophene having formula (5) obtained as reported above, and 60 ml of a mixture of chloroform and acetic acid (1:1 vol.). 0.63 g (3.6 mmol) of N-bromosuccinimide (NBS) were added, in small portions, to the resulting solution, at 0° C. The resulting reaction mixture was stirred at room temperature (25° C.), for 3 hours, and subsequently poured into water and extracted with dichloromethane (CH$_2$Cl$_2$) (3×20 ml). The overall organic phase (obtained by joining the organic phases obtained as described above) is thoroughly washed with water, aqueous sodium bicarbonate, brine and again with water, and subsequently dried over anhydrous magnesium sulfate (MgSO$_4$). The solvent was subsequently evaporated at reduced pressure and the obtained residue was purified by chromatography on silica gel using petroleum ether as eluent obtaining 1.61 g (93% yield) of 5,5''''-dibromo-3,3',3''', 3''''-tetraoctyl-2,5':2',5'':2'',2''':5''',2''''-pentathiophene having formula (6), as a yellow oil, which was characterized by $^1$H NMR (300 MHz, CDCl$_3$) obtaining the following spectrum: 7.07 (s, 2H), 6.88 (s, 4H), 2.77 (t, 4H), 2.71 (t, 4H), 1.66-1.58 (m, 8H), 1.29-1.26 (m, 40H), 0.90 (m, 12H).

In a 100 ml flask, were introduced 1.61 g (1.6 mmol) of 5,5'-dibromo-3,3',3''',3''''-tetraoctyl-2,5':2',5'':2'',2''':5''',2''''-pentathiophene having formula (6) obtained as reported above, 0.09 g (0.16 mmol) of [1,3-bis(diphenylphosphino)propane]dichloronickel(II) [Ni(DPPP)Cl$_2$] and 30 ml of anhydrous diethyl ether. To the resulting solution were added, dropwise, 30 ml of an anhydrous diethyl ether solution containing 4.7 mmol of 2-(3-octylthienyl)magnesium bromide having formula (2) obtained as reported above. The resulting reaction mixture was heated at the boiling point of the solvent, for 20 hours, subsequently cooled to room temperature (25° C.) and quenched with 10 ml of hydrochloric acid (HCl) (1 M), followed by the addition of 50 ml of water. The obtained mixture was extracted with dichloromethane (CH$_2$Cl$_2$) (3×20 ml), and the overall organic phase (obtained by joining the organic phases obtained as described above) were washed with water, brine and dried over anhydrous magnesium sulfate (MgSO$_4$). The solvent was subsequently evaporated at reduced pressure and the obtained residue was purified by chromatography on silica gel using petroleum ether as eluent obtaining 1.5 g (75% yield) of 3,3',3'',3''',3'''',3'''''-hexaoctyl-2,5':2',5'':2'',2''':5''',2'''':5'''',2''''':5''''',2''''''-heptathiophene having formula (7), as a brick red solid which was characterized by $^1$H NMR (300 MHz, CDCl$_3$) obtaining the following spectrum: 7.17 (d, 2H), 7.09 (s, 2H), 6.97 (s, 2H), 6.94 (s, 2H), 6.94 (d, 2H), 2.81-2.76 (m, 12H), 1.69-1.67 (m, 12H), 1.30-1.28 (m, 60H), 0.90-0.83 (m, 18H).

In a 100 ml flask, were introduced 1.04 g (0.83 mmol) of 3,3',3'',3''',3'''',3'''''-hexaoctyl-2,5':2',5'':2'',2''':5''',2'''':5'''',2''''':5''''',2''''''-heptathiophene having formula (7) obtained as reported above and 15 ml of 1,2-dichloroethane. The resulting solution was cooled at 0° C. and a Vilsmeier reagent, which was prepared adding 0.09 ml (0.99 mmol) of phosphorous oxychloride (POCl$_3$) in 0.07 ml (0.99 mmol) of dry dimethylformamide (DMF) was subsequently added under an argon (Ar) atmosphere. The obtained reaction mixture was stirred at 60° C., for 12 hours, subsequently cooled to room temperature (25° C.) and diluted with 25 ml of dichloromethane (CH$_2$Cl$_2$). The obtained reaction mixture was treated with 50 ml of an aqueous solution of sodium acetate and stirred for 2 hours, at room temperature (25° C.), obtaining an organic phase and an aqueous phase which were separated. The organic phase was washed with water, brine and dried over anhydrous magnesium sulfate (MgSO$_4$). The solvent was subsequently evaporated at reduced pressure and the obtained residue was purified by chromatography on silica gel using a mixture of dichloromethane (CH$_2$Cl$_2$) and petroleum ether (1:1) as eluent obtaining 0.61 g (59% yield) of 5-formyl-3,3',3'',3''',3'''',3'''''-hexaoctyl-2,5':2',5'':2'',2''':5''',2'''':5'''',2''''':5''''',2''''''-heptathiophene having formula (8), as reddish solid, which was characterized by $^1$H NMR (300 MHz, CDCl$_3$) obtaining the following spectrum: 9.82 (s, 1H), 7.58 (s, 1H), 7.17 (d, 1H), 7.13 (s, 1H), 7.11 (s, 2H), 7.01 (s, 1H), 6.98 (s, 1H), 6.94 (s, 1H), 6.92 (d, 1H), 2.85-2.76 (m, 12H), 1.72-1.68 (m, 12H), 1.39-1.28 (m, 60H), 0.90-0.86 (m, 18H).

In a 100 ml flask, were introduced 0.04 g (0.47 mmol) of cyanoacetic acid, 0.05 g (0.71 mmol) of ammonium acetate and 50 ml of glacial acetic acid. To the resulting solution were added 0.61 g (0.49 mmol) of 5-formyl-3,3',3'',3''',3'''',3'''''-hexaoctyl-2,5':2',5'':2'',2''':5''',2'''':5'''',2''''':5''''',2''''''-heptathiophene having formula (8) obtained as reported above and the reaction mixture was heated at the boiling point of the solvent, for 12 hours. After cooling to room temperature (25° C.), the resulting mixture was poured into 100 ml of water, extracted with dichloromethane (CH$_2$Cl$_2$) (3×30 ml) and the combined organic phases were dried over anhydrous magnesium sulfate (MgSO$_4$). The solvent was subsequently evaporated at reduced pressure and the obtained dark red residue was solved in 2 ml of dichloromethane (CH$_2$Cl$_2$) and precipitated by adding 20 ml of methanol (MeOH). The obtained dark precipitate was purified by chromatography on silica gel using first dichloromethane (CH$_2$Cl$_2$) and subsequently methanol (MeOH) as eluents obtaining 0.35 g (53% yield) of 5-carboxycyanovinylene-3,3',3'',3''',3'''',3'''''-hexaoctyl-2,5':2',5'':2'',2''':5''',2'''':5'''',2''''':5''''',2''''''-heptathiophene having formula (Ia) as reddish oil, which was characterized by $^1$H NMR (300 MHz, CDCl$_3$) obtaining the following spectrum: 8.09 (s, 1H) 7.43 (s, 1H), 7.16 (d, 1H), 7.09 (s, 2H), 6.99 (m, 2H), 6.93 (m, 2H), 2.87-2.80 (m, 12H), 1.68-1.65 (m, 12H), 1.37-1.27 (m, 60H), 0.89-0.85 (m, 18H).

Said compound of formula (Ia) was also characterized by mass spectra: HRMS (ESI) obtaining: [M-H]: 1342.6742, and MALDI obtaining: [M]: 1343.6; calculated for C$_{80}$H$_{113}$NO$_2$S$_7$: 1343.6816.

Example 2

Preparation of Dye-Sensitized Solar Cell (DSSC)

Titanium dioxide (TiO$_2$) electrodes were prepared by spreading ("doctor-blade" technique) a colloidal paste containing a 20 nm sized titanium dioxide (TiO$_2$) particles (TiO$_2$ Paste DSL 18NR-T-Dyesol) on a conductive FTO glass (Hartford Glass Co., TEC 8, having a thickness of 2.3 mm and a sheet resistance of 6 Ω/cm$^2$-9 Ω/cm$^2$), previously cleaned with water and ethanol, immersed in a freshly prepared aqueous titanium tetrachloride (TiCl$_4$) solution (4.5×10$^{-2}$ M), at 70° C., for 30 minutes, and finally washed with ethanol.

After a first drying at 125° C., for 15 minutes, a reflecting scattering layer containing >100 nm sized titanium dioxide (TiO$_2$) particles (Ti-Nanoxide R/SP-Solaronix) was spread ("doctor-blade" technique) over the first titanium dioxide (TiO$_2$) layer and sintered till 500° C., for 30 minutes. The titanium dioxide (TiO$_2$) film-coated glass was cooled to room temperature (25° C.) and immersed again in a freshly prepared aqueous titanium tetrachloride (TiCl$_4$) solution (4.5×10$^{-2}$ M), at 70° C., for 30 minutes, finally washed with ethanol and sintered at 500° C., for 30 minutes, obtaining a final thickness of the electrode of 12 μm.

After sintering, the titanium dioxide (TiO$_2$) film-coated glass was cooled at about 80° C.-100° C. and immediately immersed into a dichloromethane (CH$_2$Cl$_2$) solution (5×10$^{-4}$ M) of the compound having formula (Ia) obtained in Example 1, at room temperature (25° C.), for 24 h. The dyed titania-glass was washed with ethanol and dried at room temperature (25° C.), under a nitrogen (N$_2$) flux.

A 50 μm thick Surlyn spacer (TPS 065093-50-Dyesol) was used to seal the photoanode obtained as disclosed above and the counter electrode constituted of a platinized FTO glass (Hartford Glass Co., TEC 8, having a thickness of 2.3 mm and a sheet resistance of 6 Ω/cm$^2$-9 Ω/cm$^2$), subsequently the cell was filled up with the electrolyte solution having the following composition: N-methyl-N-butylimidazolium iodide (0.6 M), iodine (0.04 M), lithium iodide (LiI) (0.025 M), guanidinium-thiocyanate (0.05 M) and tert-butylpyridine (0.28 M), in a 15:85 (v/v) mixture of valeronitrile and acetonitrile.

The active area of the cell, calculated by means of a microphotography, was 0.1435 cm$^2$.

The photovoltaic performance of the cell was measured with a solar simulator (Abet 2000) equipped with a 300 W Xenon light source, the light intensity was adjusted with a standard calibrated Si solar cell ("VLSI Standard" SRC-1000-RTD-KGS), the current-voltage characteristics were acquired by applying an external voltage to the cell and measuring the generated photocurrent with a "Keithley 2602A" (3 A DC, 10 A Pulse) digital source meter. The following results were obtained:

Voc (open circuit photovoltage)=723 mV;
FF (fill factor)=69.3%;
Jsc (short-circuit photocurrent density)=18.33 mA/cm$^2$;
η (photoelectric transformation efficiency)=9.18%.

The invention claimed is:

1. Organic dye having general formula (I):

$$X-(T)_n-Y-(T)_n-Z \quad (I)$$

wherein:
X and Z, equal to or different from each other, represent a hydrogen atom; or are selected from the following groups: a —COOH group, a carboxycyanovinylene group having formula (II) or (III):

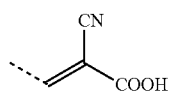

(II)

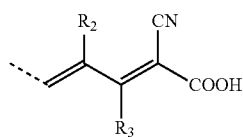

(III)

wherein $R_2$ and $R_3$, equal to or different from each other, represent an hydrogen atom, or are selected from $C_1$-$C_{16}$ alkyl groups linear or branched; with the provision that at least one of X and Z is not an hydrogen atom;

T represents a 2,5-thienylene group having general formula (IV):

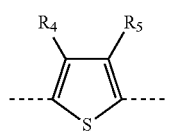

(IV)

wherein $R_4$ and $R_5$, equal to or different from each other, represent an hydrogen atom; or are selected from: $C_4$-$C_{20}$ alkyl groups, linear or branched, saturated or unsaturated, optionally containing heteroatoms, $C_4$-$C_{12}$ cycloalkyl groups, optionally substituted, $C_4$-$C_{11}$ heterocyclic groups, optionally substituted, $C_3$-$C_{20}$ trialkylsilyl groups; with the provision that at least one of $R_4$ and $R_5$ is not an hydrogen atom;

n is an integer ranging from 2 to 7;

Y represents a divalent organic aromatic or heteroaromatic group having electron-donor properties selected from the group consisting of the following groups having general formulae (V), (VI), (VII), (IX), (X), (XI), (XII), (XIII), (XIV), (XV), (XVI), (XVII), (XVIII), (XIX):

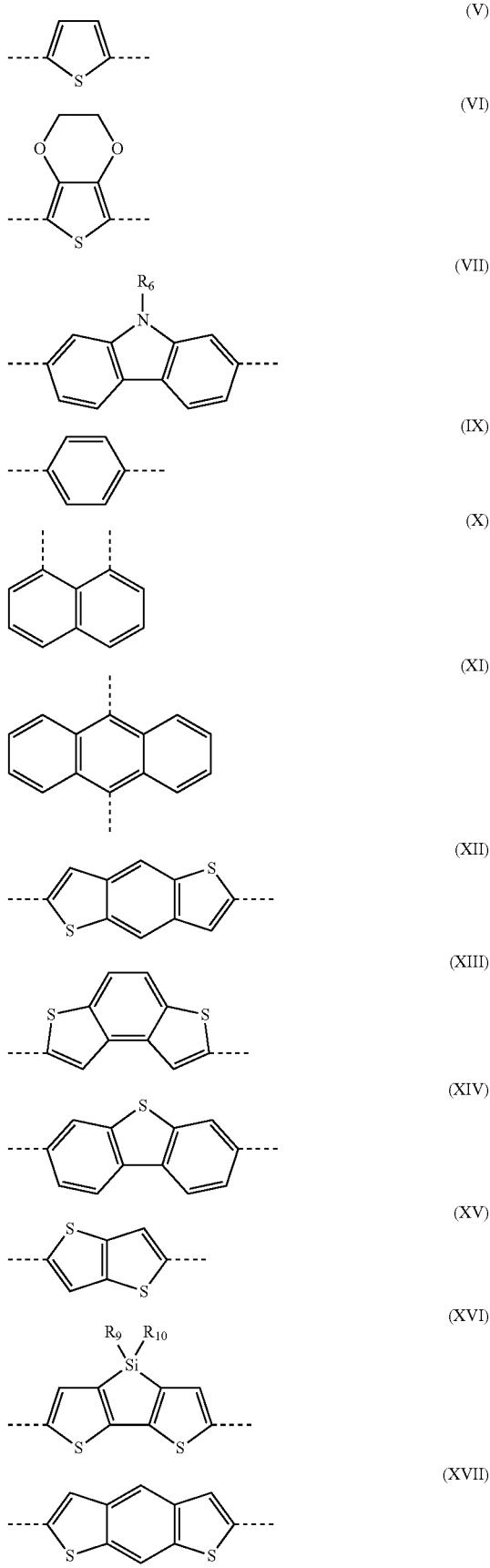

-continued (XVIII)

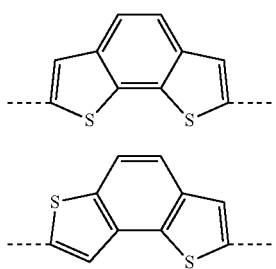

(XIX)

wherein $R_6$, $R_9$ and $R_{10}$, equal to or different from each other, represent an hydrogen atom; or are selected from: $C_1$-$C_{30}$ alkyl groups, linear or branched, saturated or unsaturated, $C_4$-$C_{12}$ cycloalkyl groups optionally substituted; said Y groups being optionally substituted with one or more group selected from $C_1$-$C_{30}$ alkyl groups, linear or branched, saturated or unsaturated, $C_4$-$C_{12}$ cycloalkyl groups optionally substituted.

2. Organic dye according to claim 1, wherein in said general formula (I):

X is a hydrogen atom;

Z is a carboxycyanovinylene group having formula (II):

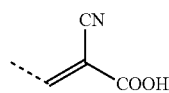
(II)

T represents a 2,5-thienylene group having general formula (IV):

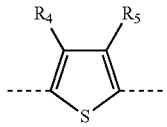
(IV)

wherein $R_4$ is a hydrogen atom and $R_5$ is a n-hexyl group or a n-octyl group;

n is 3;

Y is a divalent heteroaromatic group having general formula (V) or (VI):

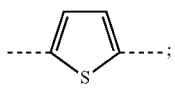
(V)

-continued

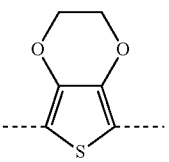
(VI)

3. Dye-sensitized photoelectric transformation element comprising at least one organic dye having general formula (I) according to claim 1, said dye-sensitized photoelectric transformation element being supported on oxide semiconductor particles.

4. Dye-sensitized solar cell comprising the dye-sensitized photoelectric transformation element according to claim 3.

5. Organic dye according to claim 1, wherein in said general formula (I):

X is a hydrogen atom;

Z is a carboxycyanovinylene group having formula (II):

(II)

T represents a 2,5-thienylene group having general formula (IV):

(IV)

wherein $R_4$ is a hydrogen atom and $R_5$ is a n-hexyl group or a n-octyl group;

n is 3;

Y is a divalent heteroaromatic group having general formula (V) or (VI):

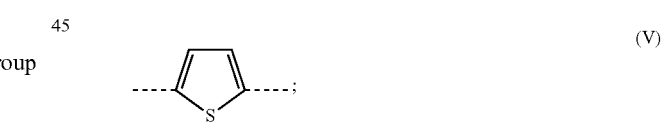
(V)

(IV)

* * * * *